US006103679A

United States Patent [19]

Van der Weerdt et al.

[11] Patent Number: 6,103,679

[45] Date of Patent: Aug. 15, 2000

[54] MACROCYCLIC MUSK MIXTURES

[75] Inventors: Antonius Johannes Albertus Van der Weerdt, Huizen, Netherlands; Ian Michael Payne, Ashford, United Kingdom

[73] Assignee: Imperial Chemical Industries PLC, United Kingdom

[21] Appl. No.: 09/354,001

[22] Filed: Jul. 15, 1999

Related U.S. Application Data

[63] Continuation of application No. PCT/GB98/00166, Jan. 20, 1998.

[30] Foreign Application Priority Data

| | | | |
|---|---|---|---|
| Jan. 24, 1997 | [EP] | European Pat. Off. | 97300457 |
| Jun. 13, 1997 | [EP] | European Pat. Off. | 97304146 |
| Jun. 23, 1997 | [EP] | European Pat. Off. | 97304402 |
| Aug. 1, 1997 | [EP] | European Pat. Off. | 97305835 |

[51] Int. Cl.[7] .................... C11D 3/50; C11D 9/44; A61K 7/30; A61K 7/40

[52] U.S. Cl. .................... 510/103; 510/119; 510/131; 510/276

[58] Field of Search .................... 510/103, 119, 510/131, 276

[56] References Cited

U.S. PATENT DOCUMENTS

| | | | |
|---|---|---|---|
| 3,925,417 | 12/1975 | Story et al. | 260/338 |

FOREIGN PATENT DOCUMENTS

| | | |
|---|---|---|
| 24 40 526 | 3/1975 | Germany . |
| 63-230 685 | 9/1988 | Japan . |
| 63-230685 | 9/1988 | Japan . |
| 03 170 403 | 7/1991 | Japan . |
| 04001189 | 1/1992 | Japan . |
| 113142 | 4/1998 | Romania . |
| 2 122 869 | 1/1984 | United Kingdom . |
| 96 29281 | 9/1996 | WIPO . |

OTHER PUBLICATIONS

Chemical Abstracts, vol. 116, No. 23, Jun. 8, 1992 Columbus, Ohio, US; abstract No. 234463, A Makita: XP002032206 see abstract & JP 04 001 189 A (Nippon Mining).

*Primary Examiner*—Necholus Ogden
*Assistant Examiner*—John M Petruncio

[57] ABSTRACT

Mixtures of at least two of the macrocyclic musk fragrances hexadecanolide, cyclopentadecanone and pentadecanolide and methods of using such mixtures are described. These mixtures possess substantivity to proteinaceous and cellulosic substrates which is significantly better than the substantivity of the separate components and are therefore very suitable for perfumes to be applied in products intended for treating skin, hair or textile fibers, such as bath and shower products, shampoos, laundry detergents, rinse conditioners, fabric softeners and the like. The mixtures are thus able to replace polycyclic musk fragrances in such products.

17 Claims, No Drawings

MACROCYCLIC MUSK MIXTURES

This is a continuation under 35 U.S.C. Section 120 of International application Ser. No. PCT/GB98/00166 filed on Jan. 20, 1998 which application designates the US.

The invention relates to mixtures of macrocyclic musks and their use as perfume materials for application to various substrates, such as textile fibers.

Musk fragrances are well known and much used perfume ingredients in perfumes for a large range of products. Perfumes for application in laundry detergents, fabric softeners, rinse conditioners and other products intended for use on textile fibers primarily contain musk fragrances of the class of polycyclic musks. Well known examples of this class are marketed under various tradenames such as Extralide, Tonalide, Traseolide, Galaxolide etc.

An important characteristic of perfume ingredients to be used in perfumes for application in laundry detergents, fabric softeners and the like is their fibre substantivity, i.e. their ability to attach to the textile fiber rather than be washed away with the wash or rinse water or evaporate in a laundry dryer. Good fibre substantive perfumes are able to give the laundry a perceivable perfume for days or weeks after the clothes have been washed and dried, whereas less substantive perfumes may be unnoticeable after a few hours.

Another important characteristic of perfume ingredients in general and those used in detergency in particular is their biodegradability. Good biodegradability of perfume ingredients prevents their undesirable accumulation in the environment Although the polycyclic musks are extensively used in perfumes for products for laundry treatment, their fibre substantivity in comparison with other perfume ingredients is variable, some are rated as good, others are reasonable or not more than moderate.

Macrocyclic musks are also long known in perfumery; well known examples of this class of perfume ingredients are cyclohexadecanone, hexadecanolide, cyclopentadecanone, pentadecanolide and various unsaturated and/or methyl substituted analogues thereof. So far the application of these compounds has been largely confined to so called "fine perfumery" i.e. perfumes for direct application to the skin or for use in a cosmetic product. Many applications in this area do not demand particular substantivity i.e. resistance to being washed or rinsed away, although for some, such as hair care products, it could be a distinct advantage. The fibre substantivity of macrocyclic musks also varies with the compound: some are rated as reasonable, most are not more than moderate. On the other hand macrocyclic musks are easily biodegradable.

It has now been found that mixtures of at least two of the macrocyclic musks hexadecanolide, cyclopentadecanone and pentadecanolide possess substantivity to cellulosic and proteinaceous substrates which is comparable to that of the more substantive polycyclic musks and at least as good as, but in most cases significantly better, than the substantivity of the separate components hexadecanolide, cyclopentadecanone and pentadecanolide to such substrates. Thus, such mixtures of at least two of hexadecanolide, cyclopentadecanone and pentadecanolide are very suitable perfume ingredients for perfumes to be applied in products intended for treating proteinaceous or cellulosic fibres, such as hair, wool and cotton or for washing or rinsing the skin.

The invention therefore provides products for treating skin, hair or textile fibres which comprise mixtures of at least two of the macrocyclic musks hexadecanolide, cyclopentadecanone and pentadecanolide, which mixtures possess enhanced substantivity and are hereinafter referred to as "musk mixtures". Preferred musk mixtures are mixtures of hexadecanolide and cyclopentadecanone and optionally pentadecanolide. Particularly preferred are mixtures of hexadecanolide and cyclopentadecanone. Products for treating the skin are e.g. bath and shower products, face washes and the like. Products for treating hair are e.g. shampoo, hair rinse conditioners and the like. Products for treating textile fibres such as laundry, clothing, fabric, etc, are laundry detergents, fabric softeners, rinse conditioners, fabric sprays, ironing aids and similar products intended for treating clothing, fabric, etc are hereinafter collectively referred to as "fibre treatment products". Preferred fibre treatment products according to the invention are those intended for treating cotton, wool and nylon, more particularly for treating cotton.

The musk mixtures according to the invention may be incorporated as such into the products according to the invention. Preferably, however, they are made part of a complete perfume which apart from the musk odour imparts many other desirable olfactory properties to the product. In such perfumes the musk mixtures are blended with many other perfume ingredients known in the art to obtain a harmonious total odour of which the musk odour is one aspect.

Thus, the invention also provides perfumes comprising the musk mixtures according to the invention. Since these macrocyclic musk mixtures are easily biodegradable and equal well known polycyclic musks in substantivity, they are able to partly or completely replace polycyclic musks in such perfumes. Therefore, perfumes containing the macrocyclic musk mixtures according to the invention, but which do not contain any polycyclic musks are specific embodiments of the invention. Other embodiments of the invention are perfumes containing the musk mixtures together with smaller amounts of polycyclic musks than would otherwise be used in such perfumes.

Furthermore, the invention provides mixtures of two or all three of the macrocyclic musks hexadecanolide, cyclopentadecanone and pentadecanolide. Mixtures of pentadecanolide and cyclopentadecanone are known in the art as reaction products of Bayer-Villiger type reactions to convert cyclopentadecanone into pentadecanolide, see JP-A-04/001189 and JP-A-63/230685. However, such mixtures have not been described as being suitable for perfumery without separating out the desired pentadecanolide. Musk mixtures of hexadecanolide and either cyclopentadecanone or pentadecanolide or both are novel. Preferred are mixtures of hexadecanolide and cyclopentadecanone and optionally pentadecanolide. Particularly preferred are mixtures of hexadecanolide and cyclopentadecanone The musk mixtures according to the invention preferably contain at most 90% by weight of each of the components. Thus, if composed of two components the mixtures preferably contain 10–90% w/w of each. More preferably they contain at most 80% w/w of each of the components, which for two component mixtures means 20–80% of each. Most preferably the mixtures contain at most 70% of each of the components. Particularly preferred are musk mixtures which contain at least hexadecanolide and cyclopentadecanone each in an amount of between 70 and 30% by weight.

Substantivity was evaluated olfactively by a panel after treating samples of substrate with a perfumed product, such as a fabric softener for cotton fabric or a shampoo for hair, containing the musk mixtures according to the invention or other musk fragrances for comparison, according to standard procedures described below. Thus, the evaluation is essentially a relative odour intensity measurement. It is known that the perceived odour intensity of mixtures of perfume ingredients when evaluated as such is generally less than the sum of the perceived odours of the components. Thus, the perceived odour intensity of a 1:1 mixture of 2 of the components of the musk mixtures according to the invention would be expected to be lower than the sum of the intensities of the separate components, i.e. in such mixtures odour suppression is generally found. In contradistinction to this the perceived odour intensity on substrate treated with the musk mixtures according to the invention is at least equal to, but in most cases greater than the perceived intensity of substrate treated with equal amounts of the separate components.

Other perfume ingredients which may be advantageously combined with the musk mixtures according to the invention in a perfume are, for example, certain natural extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such perfume ingredients are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1997", Allured Publishing Co. Wheaton, Ill. USA, or earlier versions of this yearly publication.

Examples of perfume ingredients which can be used in combination with the musk mixtures according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl) propanal, 3-(p-tert-butylphenyl)propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxy-citronellal, ionones, methylionones, isomethylionones, irones, cis-3-hexenol and esters thereof, indan musks, tetralin musks, isochroman musks.

The quantities in which the musk mixtures according to the invention can be used in perfumes or in products to be perfumed may vary within wide limits and depend, inter alia, on the precise nature of the product, on the nature and the quantity of the other components of the perfume in which the musk mixture is used and on the olfactive effect desired. It is therefore only possible to specify wide limits, which, however, provide sufficient information for the specialist in the art to be able to use the musk mixtures according to the invention for his specific purpose. In perfumes an amount of 0.01% by weight or more of the musk mixtures according to the invention will generally have a perceptible olfactive effect. Preferably the amount is at least 0.1% by weight, more preferably at least 0.5%. The amount of the musk mixtures according to the invention present in products will generally be at least 10 ppm by weight, preferably at least 50 ppm, more preferably at least 100 ppm.

The invention is further illustrated in the examples below.

EXAMPLE 1

Comparison of the fibre substantivity of single polycyclic musks and macrocyclic musks with musk mixtures according to the invention.

70% Solutions in isopropyl myristate of the musks and musk mixtures to be tested were dosed at 0.25% w/w in a single Arquad fabric softener (GT 117B). The tests were carried out by rinsing "6"×6" (weight: 16 g) cotton terry towelling pieces at ambient temperature in a tergotometer according to the procedure below:

3 g of fabric softener containing the test musk was added to 1 liter of water and agitated for one minute to disperse. The fabric piece was added and washed for 10 minutes with constant agitationat 100 rpm. On completion of the wash cycle the pieces were hand wringed and line dried for 20 hours.

The cloths were assessed olfactively by an 14 membered panel. A ten point scale was used running from 9 (very good) to 0 (very poor). The results are presented below in Table 1:

TABLE 1

| Musk | Rating | Standard deviation |
|---|---|---|
| Musk mixture 1* | 6.9 | 1.5 |
| Hexadecanolide | 4.8 | 2.1 |
| Cyclopentadecanone | 5.9 | 2.9 |
| Tonalid** | 7.2 | 1.5 |
| Galaxolide*** | 3.8 | 2.3 |

*The musk mixture consisted of 50% hexadecanolide and 50% cyclopentadecanone.
**Trademark for a polycyclic musk marketed by PFW.
***Trademark for a polycyclic musk marketed by IFF.

EXAMPLE 2

The procedure of Example 1 was repeated using mixtures comprising cyclopentadecanolide with one or both of the other macrocyclic musks in equal amounts as compared with cyclopentadecanolide alone and with Tonalid. The results are presented below in Table 2:

TABLE 2

| Musk | Rating | Standard deviation |
|---|---|---|
| Pentadecanolide/ cyclopentadecanone | 5.2 | 2.8 |
| Pentadecanolide/ hexadecanolide | 5.7 | 2.1 |
| Pentadecanolide/ cyclopentadecanone/ hexadecanolide | 6.5 | 1.4 |

TABLE 2-continued

| Musk | Rating | Standard deviation |
|---|---|---|
| Cyclopentadecanolide | 3.2 | 2.0 |
| Tonalide | 6.7 | 1.4 |

EXAMPLE 3

The procedure of Example 1 was repeated using identical pieces of woolen cloth. The cloths were assessed olfactively by an 9 membered panel before and after line drying, i.e. damp and dry. The odours were assesed relative to the odour of the cloth treated with Tonalid which was arbitrarily give the value 10 The results are presented below in Table 3A and B:

TABLE 3

| Musk | Rating | Standard deviation |
|---|---|---|
| A (damp) | | |
| Musk mixture 1 | 10.0 | 3.9 |
| Hexadecanolide | 5.8 | 4.0 |
| Cyclopentadecanone | 9.4 | 4.5 |
| Tonalid | 10 | 0 |
| B (dry) | | |
| Musk mixture 1 | 9.8 | 3.8 |
| Hexadecanolide | 6.4 | 3.0 |
| Cyclopentadecanone | 6.1 | 4.2 |
| Tonalid | 10 | 0 |

EXAMPLE 4

Comparison of the hair substantivity of a single polycyclic musk, two macrocyclic musks and a 50/50 mixture of these two.

The perfume ingredients to be tested were dosed at 0.3% w/w in an unperfumed shampoo base. The tests were carried out by washing hair switches each weighing 10 g in equal shampoo solutions each containing 0.2 of shampoo for 30 sec The lathered switches were left for 1 minute and then rinsed for 15 sec under running tap water. The switches were subsequently line dried in an odour free atmosphere for eighteen hours prior to olfactively assessment One hair switch was treated the same way, but with unperfumed shampoo as control.

The hair switches were assessed olfactively by a 13 membered panel. A ten point scale was used running from 1 (very poor) to 10 (very good): The results are presented below in TABLE 4

TABLE 4

| Musk | Rating | Standard deviation |
|---|---|---|
| Hexadecanolide | 5.2 | 1.4 |
| Cyclopentadecanonone/ hexadecanolide | 5.0 | 1.0 |

TABLE 4-continued

| Musk | Rating | Standard deviation |
|---|---|---|
| Cyclopentadecanone | 2.8 | 1.7 |
| Galaxolide | 4.9 | 1.6 |

We claim:

1. A method of treating skin, hair or textile fibers comprising applying a musk mixture of at least two macrocyclic musks selected from the group consisting of hexadecanolide, cyclopentadecanone, and pentadecanolide to said skin, hair or textile fibers.

2. A method according to claim 1 wherein the musk mixture contains at most 90% w/w of each of the macrocyclic musks.

3. A method according to claim 1 wherein the musk mixture contains at most 80% w/w of each of the macrocyclic musks.

4. A method according to claim 1 wherein the musk mixture comprises at least hexadecanolide and cyclopentadecanone.

5. A method according to claim 4 wherein the musk mixture further comprises pentadecanolide.

6. A method according to claim 1 wherein the musk mixture is part of a perfume.

7. A perfume which comprises a musk mixture of at least two macrocyclic musks selected from the group consisting of hexadecanolide, cyclopentadecanone and pentadecanolide.

8. A perfume according to claim 7 wherein the musk mixture contains at most 90% w/w of each of the macrocyclic musks.

9. A perfume according to claim 8 wherein the musk mixture contains at most 80% w/w of each of the macrocyclic musks.

10. A perfume according to claim 7 wherein the musk mixture comprises hexadecanolide and cyclopentadecanone.

11. A perfume according to claim 10 wherein the musk mixture further comprises pentadecanolide.

12. A perfume according to claim 7 wherein the musk mixture comprises at least 0.01% of the perfume.

13. A perfume according to claim 7 wherein the musk mixture further comprises at least one additional perfume ingredient.

14. A musk mixture which comprises hexadecanolide with one or both of cyclopentadecanone and pentadecanolide.

15. A musk mixture according to claim 14 comprising hexadecanolide and cyclopentadecanone.

16. A musk mixture according to claim 15 which further comprises pentadecanolide.

17. A musk mixture according to claim 15 wherein hexadecanolide and cyclopentadecanone are present in a ratio of 1:1.

* * * * *